(12) United States Patent
Ghose et al.

(10) Patent No.: US 11,347,844 B2
(45) Date of Patent: May 31, 2022

(54) DATA SECURITY IN BIOINFORMATIC SEQUENCE ANALYSIS

(71) Applicant: Seven Bridges Genomics, Inc., Charlestown, MA (US)

(72) Inventors: Kaushik Ghose, Malden, MA (US); Deniz Kurai, Somerville, MA (US)

(73) Assignee: Seven Bridges Genomics, Inc., Charlestown, MA (US)

( * ) Notice: Subject to any disclaimer, the term of this patent is extended or adjusted under 35 U.S.C. 154(b) by 927 days.

(21) Appl. No.: 15/907,847

(22) Filed: Feb. 28, 2018

(65) Prior Publication Data

US 2018/0253553 A1 Sep. 6, 2018

Related U.S. Application Data

(60) Provisional application No. 62/465,459, filed on Mar. 1, 2017.

(51) Int. Cl.
| | |
|---|---|
| *G01N 33/48* | (2006.01) |
| *G01N 33/50* | (2006.01) |
| *G06F 21/55* | (2013.01) |
| *G16B 30/00* | (2019.01) |
| *G16B 50/00* | (2019.01) |
| *G16B 30/10* | (2019.01) |

(52) U.S. Cl.
CPC ........... *G06F 21/554* (2013.01); *G16B 30/00* (2019.02); *G16B 30/10* (2019.02); *G16B 50/00* (2019.02); *G06F 2221/032* (2013.01)

(58) Field of Classification Search
CPC . G06F 21/554; G06F 2221/032; G16B 30/10; G16B 50/00; G16B 30/00
See application file for complete search history.

(56) References Cited

U.S. PATENT DOCUMENTS

| | | |
|---|---|---|
| 5,511,158 A | 4/1996 | Sims |
| 5,701,256 A | 12/1997 | Marr et al. |
| 6,054,278 A | 4/2000 | Dodge et al. |

(Continued)

FOREIGN PATENT DOCUMENTS

| | | |
|---|---|---|
| WO | 2012096579 A3 | 7/2012 |
| WO | 2012098515 A1 | 7/2012 |

(Continued)

OTHER PUBLICATIONS

Shajii et al. Fast genotyping of known SNPs through approximate k-mer matching. Bioinformatics, vol. 32, Aug. 29, 2016, pp. i538-i544.*

(Continued)

*Primary Examiner* — Russell S Negin
(74) *Attorney, Agent, or Firm* — Morgan, Lewis & Bockius LLP

(57) ABSTRACT

Systems and methods for protecting information stored in private references that are available to be queried—e.g., graph-based sequence references that users query through an interface, providing short reads to obtain the results of an alignment against the reference sequence—analyze the query and/or alignment results to determine whether the query represents an attack. The analysis may be performed before returning results to a user, and in some cases before performing the alignment.

17 Claims, 6 Drawing Sheets

(56) References Cited

U.S. PATENT DOCUMENTS

| | | |
|---|---|---|
| 6,223,128 B1 | 4/2001 | Allex et al. |
| 7,577,554 B2 | 8/2009 | Lystad et al. |
| 7,580,918 B2 | 8/2009 | Chang et al. |
| 7,809,509 B2 | 10/2010 | Milosavljevic |
| 7,885,840 B2 | 2/2011 | Sadiq et al. |
| 7,917,302 B2 | 3/2011 | Rognes |
| 8,209,130 B1 | 6/2012 | Kennedy et al. |
| 8,340,914 B2 | 12/2012 | Gatewood et al. |
| 8,370,079 B2 | 2/2013 | Sorenson et al. |
| 8,639,847 B2 | 1/2014 | Blaszczak et al. |
| 9,063,914 B2 | 6/2015 | Kural et al. |
| 9,092,402 B2 | 7/2015 | Kural et al. |
| 9,116,866 B2 | 8/2015 | Kural |
| 9,203,791 B1 * | 12/2015 | Olomskiy ............... G06F 21/82 |
| 9,390,226 B2 | 7/2016 | Kural |
| 9,817,944 B2 | 11/2017 | Kural |
| 2004/0023209 A1 | 2/2004 | Jonassen |
| 2005/0089906 A1 | 4/2005 | Furuta et al. |
| 2006/0292611 A1 | 12/2006 | Berka et al. |
| 2007/0166707 A1 | 7/2007 | Schadt et al. |
| 2008/0077607 A1 | 3/2008 | Gatawood et al. |
| 2008/0294403 A1 | 11/2008 | Zhu et al. |
| 2009/0119313 A1 | 5/2009 | Pearce |
| 2009/0164135 A1 | 6/2009 | Brodzik et al. |
| 2009/0300781 A1 | 12/2009 | Bancroft et al. |
| 2010/0041048 A1 | 2/2010 | Diehl et al. |
| 2010/0169026 A1 | 7/2010 | Sorenson et al. |
| 2011/0004413 A1 | 1/2011 | Carnevali et al. |
| 2011/0098193 A1 | 4/2011 | Kingsmore et al. |
| 2012/0041727 A1 | 2/2012 | Mishra et al. |
| 2012/0045771 A1 | 2/2012 | Beier et al. |
| 2012/0239706 A1 | 9/2012 | Steinfadt |
| 2012/0330566 A1 | 12/2012 | Chaisson |
| 2013/0059738 A1 | 3/2013 | Leamon et al. |
| 2013/0059740 A1 | 3/2013 | Drmanac |
| 2013/0073214 A1 | 3/2013 | Hyland et al. |
| 2013/0124100 A1 | 5/2013 | Drmanac et al. |
| 2013/0289099 A1 | 10/2013 | Goff et al. |
| 2013/0311106 A1 | 11/2013 | White et al. |
| 2014/0025312 A1 | 1/2014 | Chin et al. |
| 2014/0051588 A9 | 2/2014 | Drmanac et al. |
| 2014/0066317 A1 | 3/2014 | Talasaz |
| 2014/0136120 A1 | 5/2014 | Colwell et al. |
| 2014/0200147 A1 | 7/2014 | Bartha et al. |
| 2014/0278590 A1 | 9/2014 | Abbassi et al. |
| 2014/0280360 A1 | 9/2014 | Webber et al. |
| 2014/0323320 A1 | 10/2014 | Jia et al. |
| 2015/0056613 A1 | 2/2015 | Kural |
| 2015/0057946 A1 | 2/2015 | Kural |
| 2015/0094212 A1 | 4/2015 | Gottimukkala et al. |
| 2015/0110754 A1 | 4/2015 | Bai et al. |
| 2015/0112602 A1 | 4/2015 | Kural et al. |
| 2015/0112658 A1 | 4/2015 | Kural et al. |
| 2015/0197815 A1 | 7/2015 | Kural |
| 2015/0199472 A1 | 7/2015 | Kural |
| 2015/0199473 A1 | 7/2015 | Kural |
| 2015/0199474 A1 | 7/2015 | Kural |
| 2015/0199475 A1 | 7/2015 | Kural |
| 2015/0227685 A1 | 8/2015 | Kural |
| 2015/0293994 A1 | 10/2015 | Kelly |
| 2015/0302145 A1 | 10/2015 | Kural et al. |
| 2015/0310167 A1 | 10/2015 | Kural et al. |
| 2015/0344970 A1 | 12/2015 | Vogelstein et al. |
| 2015/0347678 A1 | 12/2015 | Kural |
| 2015/0356147 A1 | 12/2015 | Mishra et al. |
| 2016/0259880 A1 | 9/2016 | Semenyuk |
| 2016/0306921 A1 | 10/2016 | Kural |
| 2016/0364523 A1 | 12/2016 | Locke et al. |
| 2017/0058320 A1 | 3/2017 | Locke et al. |
| 2017/0058341 A1 | 3/2017 | Locke et al. |
| 2017/0058365 A1 | 3/2017 | Locke et al. |
| 2017/0198351 A1 | 7/2017 | Lee et al. |
| 2017/0199959 A1 | 7/2017 | Locke |
| 2017/0199960 A1 | 7/2017 | Ghose et al. |
| 2017/0242958 A1 | 8/2017 | Brown |

FOREIGN PATENT DOCUMENTS

| | | |
|---|---|---|
| WO | 2012142531 A2 | 10/2012 |
| WO | 2015027050 A1 | 2/2015 |
| WO | 2015048753 A1 | 4/2015 |
| WO | 2015058093 A1 | 4/2015 |
| WO | 2015058095 A1 | 4/2015 |
| WO | 2015058097 A1 | 4/2015 |
| WO | 2015058120 A1 | 4/2015 |
| WO | 2015061099 A1 | 4/2015 |
| WO | 2015061103 A1 | 4/2015 |
| WO | 2015105963 A1 | 7/2015 |
| WO | 2015123269 A1 | 8/2015 |
| WO | 2016141294 A1 | 9/2016 |
| WO | 2016201215 A1 | 12/2016 |
| WO | 2017120128 A1 | 7/2017 |
| WO | 2017123864 A1 | 7/2017 |
| WO | 2017147124 A1 | 8/2017 |

OTHER PUBLICATIONS

Wang, 2009, RNA-Seq: a revolutionary tool for transcriptomics, Nat Rev Genet 10(1):57-63.
Written Opinion issued in SG 11201601124Y.
Written Opinion issued in SG 11201602903X.
Written Opinion issued in SG 11201603039P.
Written Opinion issued in SG 11201603044S.
Written Opinion issued in SG 11201605506Q.
Wu, 2010, Fast and SNP-tolerant detection of complex variants and splicing in short reads, Bioinformatics, 26 (7):873-881.
Xing, 2006, An expectation-maximization algorithm for probabilistic reconstructions of full-length isoforms from splice graphs, Nucleic Acids Research, 34:3150-3160.
Yang, 2013, Leveraging reads that span multiple single nucleotide polymorphisms for haplotype inference from sequencing data, Bioinformatics 29(18):2245-2252.
Yanovsky, 2008, Read mapping algorithms for single molecule sequencing data, Proc 8th Int Workshop Alg Bioinformatics 5251:38-49.
Yu, 2010, The construction of a tetrapioid cotton genome wide comprehensive reference map, Genomics 95:230-240.
Zeng, 2013, PyroHMMvar: a sensitive and accurate method to call short indels and SNPs for Ion Torrent and 454 data, Bioinformatics 29:22 2859-2868.
Zhang et al., Construction of a high-density genetic map for sesame based on large scale marker development by specific length amplified fragment (SLAF) sequencing. (2013) pp. 1-12, vol. 13, BMC Plant Biology.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
Newman, 2013, Community detection and graph portioning, Europhys Lett 103(2):28003, arXiv:1305.4974v1.
Newman, 2014, An ultrasensitive method for quantitating circulating tumor DNA with broad patient coverage, Nature Medicine 20:5 1-11.
Olsson, 2015, Serial monitoring of circulating tumor DNA in patients with primary breast cancer for detection of occult metastatic disease, EMBO Molecular Medicine 7:8 1034-1047.
Oshlack, 2010, From RNA-seq reads to differential expression results. Genome Bio 11:220.
Parks, 2015, Detecting non-allelic homologous recombination from high-throughput sequencing data, Genome Biol 16:17.
Peixoto, 2014, Efficient Monte Carlo and greedy heuristic for the inference of stochastic block models, Phys. Rev. E 89, 012804.
Pop et al.,, 2004, Comparative genome assembly, Briefings in Bioinformatics vol. 5, pp. 237-248.
Pruesse, 2012, SINA: Accurate high-throughput multiple sequence alignment of ribosomal RNA genes, Bioinformatics 28:14 1823-1829.

(56) References Cited

OTHER PUBLICATIONS

Rajaram, 2013, Pearl millet [*Pennisetum glaucum* (L.) R. Br.] consensus linkage map constructed using four RIL mapping populations and newly developed EST-SSRs, BMC Genomics 14(1):159.
Raphael, 2004, A novel method for multiple alignment of sequences with repeated and shuffled elements, Genome Res 14:2336-2346.
Robertson, 2010, De novo assembly and analysis of RNA-seq data, Nat Meth 7(11):909.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Roqnes, 2001, ParAlign: a parallel sequence alignment algorithm for rapid and sensitive database searches, Nucl Ac Res 29(7):1647-1652.
Rognes, 2011, Faster Smith-Waterman database searches with inter-sequence SIMD parallelisation, Bioinformatics 12:221.
Ronquist, 2012, MrBayes 3.2: efficient Bayesian phylogenetic inference and model choice across a large model space, Syst Biol 61(3):539-42.
Saebo, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central) Bioinformatics 9(318).
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions, Disc Appl Mat 127:95-117.
Tarhio, 1993, Approximate Boyer-Moore String Matching, SIAM J Comput 22(2):243-260.
Thomas, 2014, Community-wide effort aims to better represent variation in human reference genome, Genome Web (11 pages).
Trapnell, 2009, TopHat: discovering splice junctions with RNA-Seq, Bioinformatics 25:1105-1111.
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated trancripts and isoform switching during cell differentiation, Nat Biotech 28(5):511-515.
Uchiyama et al., CGAT: a comparative genome analysis tool for visualizing alignments in the analysis of complex evolutionary changes between closely related genomes, 2006, e-pp. 1-17, vol. 7:472; BMC Bioinformatics.
Agarwal, 2013, SINNET: Social Interaction Network Extractor from Text, Proc IJCNLP 33-36.
Aguiar, 2012, HapCompass: A fast cycle basis algorithm for accurate haplotype assembly of sequence data, J Comp Biol 19(6):577-590.
Aguiar, 2013, Haplotype assembly in polyploid genomes and identical by descent shared tracts, BioInformatics 29(13):i352-i360.
Airoldi, 2008, Mixed membership stochastic blockmodels, JMLR 9:1981-2014.
Albers, 2011, Dindel: Accurate indel calls from short-read data, Genome Research 21:961-973.
Alioto et al., A comprehensive assessment of somatic mutation detection in cancer using whole-genome sequencing, Nature Communications, Dec. 9, 2015.
Caboche et al., Comparison of mapping algorithms used in high-throughput sequencing: application to Ion Torrent data, 2014, vol. 15, BMC Genomics.
Cartwright, DNA assembly with gaps (DAWG): simulating sequence evolution, 2005, pp. iii31-iii38, vol. 21, Oxford University Press.
Chang, 2005, The application of alternative splicing graphs in quantitative analysis of alternative splicing form from EST database, Int J Comp Appl Tech 22(1):14.

Chin, 2013, Nonhybrid finished microbial genome assemblies from long-read SMRT sequencing data, Nat Meth 10(6):563-569.
Chuang, 2001, Gene recognition based on DAG shortest paths, Bioinformatics 17(Suppl. 1):s56-s64.
Compeau, 2011, How to apply de Bruijn graphs to genome assembly, Nat Biotech 29(11):987-991.
Craig, 1990, Ordering of cosmid clones covering the Herpes simplex virus type I (HSV-I) genome: a test case for fingerprinting by hybridisation, Nucleic Acids Research 18:9 pp. 2653-2660.
Denoeud, 2004, Identification of polymorphic tandem repeats by direct comparison of genome sequence from different bacterial strains: a web-based resource, BMC Bioinformatics 5:4 pp. 1-12.
DePristo, 2011, A framework for variation discovery and genotyping using next-generation DNA sequencing data, Nat Gen 43:491-498.
Duan et al., Optimizing de novo common wheat transcriptome assembly using short-read RNA-Seq data. (2012) pp. 1-12, vol. 13, BMC Genomics.
Dudley, 2009, A quick guide for developing effective bioinformatics programming skills, PLoS Comput Biol 5(12):e1000589.
Durbin, 2014, Efficient haplotype matching and storage using the positional Burrows-Wheeler transform (PBWT), Bioinformatics 30(9):1266-1272.
Endelman, 2011, New algorithm improves fine structure of the barley consensus SNP map, BMC Genomics 12(1):407 (and whole document).
Exam Report issued in EP14803268.3.
Examination Report issued in SG 11201601124Y.
Extended European Search Report issued in EP 14837955.5.
Extended European Search Report issued in EP 14847490.1.
Extended European Search Report issued in EP 14854801.9.
Farrar, 2007, Striped Smith-Waterman speeds database searches six times over other SIMD implementations, Bioinformatics 23(2):156-161.
Fitch, 1970, Distinguishing homologous from analogous proteins, Systematic Zoology 19:99-113.
Flicek, 2009, Sense from sequence reads: methods for alignment and assembly, Nat Meth Suppl 6(11s):s6-s12.
Florea, 2013, Genome-guided transcriptome assembly in the age of next-generation sequencing, IEEE/ACM Trans Comp Biol Bioinf 10(5):1234-1240.
Garber, 2011, Computational methods for transcriptome annotation and quantification using RNA-Seq, Nat Meth 8(6):469-477.
Gerlinger, 2012, Intratumor Heterogeneity and Branched Evolution Revealed by Multiregion Sequencing, 366:10 883-892.
Golub, 1999, Molecular classification of cancer: class discovery and class prediction by gene expression monitoring, Science 286, pp. 531-537.
Gotoh, 1982, An Improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29(7):644-654.
Grasso, 2004, Combining partial order alignment and progressive multiple sequence alignment increases alignment speed and scalability to very large alignment problems, Bioinformatics 20(10):1546-1556.
Guttman, 2010, Ab initio reconstruction of cell type-specific transcriptomes in mouse reveals the conserved multi-exonic structure of lincRNAs, Nat Biotech 28(5):503-510.
Guttman, 2010, Ab initio reconstruction of transcriptomes of pluripotent and lineage committed cells reveals gene structures of thousands of lincRNAs, NIH-PA Author Manuscript.
Haas, 2004, DAGchainer: a tool for mining segmental genome duplications and synteny, Bioinformatics 20(18):3643-3646.
Harrow, 2012, GENCODE: The reference human genome annotation for The ENCODE Project, Genome Res 22:1760-1774.
He, 2010, Optimal algorithms for haplotype assembly from whole-genome sequence data, Bioinformatics 26:i183-i190.
Heber, 2002, Splicing graphs and EST assembly problems, Bioinformatics 18 Suppl:181-188.

(56) References Cited

OTHER PUBLICATIONS

Hein, 1989, A new method that simultaneously aligns and reconstructs ancestral sequences for any number of homologous sequences when the phylogeny is given, Mol Biol Evol 6(6):649-668.
Hein, 1989, A tree reconstruction method that is economical in the number of pairwise comparisons used, Mol Biol Evol 6(6):649-668.
Homer, 2010, Improved variant discovery through local re-alignment of short-read next generation sequencing data using SRMA, Genome Biol 11(10):R99.
Horspool, 1980, Practical Fast Searching in Strings, Software-Practice & Experience 10:501-506.
Huang, Chapter 3: Bio-Sequence Comparison and Alignment, ser. Curr Top Comp Mol Biol. Cambridge, Mass.: The MIT Press, 2002.
Hutchinson, 2014, Allele-specific methylation occurs at genetic variants associated with complex diseases, PLoS One 9(e):e98464.
International Search Report and Written Opinion dated Aug. 31, 2017, for International Application No. PCT/US2017/018830 with International Filing Date Feb. 22, 2017, (11 pages).
International Search Report and Written Opinion dated Mar. 31, 2015 for International Application No. PCT/US2015/010604 filed Jan. 8, 2015 (13 pages).
International Search Report and Written Opinion dated Apr. 19, 2017 for International Patent Application No. PCT/US2017/012015, (14 Pages).
International Search Report and Written Opinion dated Feb. 17, 2015, for International Patent Application No. PCT/US2014/061156, filed Oct. 17, 2014 (19 pages).
International Search Report and Written Opinion dated Jan. 10, 2017, for International Patent Application No. PCT/US16/57324 with International Filing Date Oct. 17, 2016, (7 pages).
International Search Report and Written Opinion dated Mar. 19, 2015, for International Application No. PCT/US2014/061162 with International Filing Date Oct. 17, 2014, (12 pages).
International Search Report and Written Opinion dated May 11, 2015, for International Patent Application No. PCT/US2015/015375 with International Filing Date Feb. 11, 2015, (12 pages).
International Search Report and Written Opinion dated May 5, 2016, for International Patent Application No. PCT/US2016/020899, wiht International Filing Date Mar. 4, 2016, (12 pages).
International Search Report and Written Opinion dated Apr. 7, 2017, for International Patent Application No. PCT/US17/13329, filed Jan. 13, 2017, (9 pages).
International Search Report and Written Opinion dated Dec. 11, 2014, for International Patent Application No. PCT/US14/52065, filed Aug. 21, 2014, (18 pages).
International Search Report and Written Opinion dated Dec. 30, 2014, for International Patent Application No. PCT/US14/58328, filed Sep. 30, 2014, (22 pages).
International Search Report and Written Opinion dated Feb. 4, 2015, for International Patent Application No. PCT/US2014/061198, filed Oct. 17, 2014, (8 pages).
International Search Report and Written Opinion dated Feb. 10, 2015, for International Patent Application No. PCT/US2014/060690, filed Oct. 15, 2014, PCT/US2014/060690 (11 pages).
International Search Report and Written Opinion dated Feb. 4, 2015, for Patent Application No. PCT/US2014/061158, filed Oct. 17, 2014, (11 pages).
International Search Report and Written Opinion dated Jan. 27, 2015, for International Patent Application No. PCT/US2014/060680, filed Oct. 215, 2014, (11 pages).

International Search Report and Written Opinion dated Sep. 2, 2016, for International Patent Application No. PCT/US2016/033201 with International Filing Date May 19, 2016, (14 pages).
International Search Report and Written Opinion dated Sep. 7, 2016, for International Application No. PCT/US2016/036873 with International filing date Jun. 10, 2016, (8 pages).
Kano, 2010, Text mining meets workflow: linking U-Compare with Taverna, Bioinformatics 26(19):2486-7.
Kehr, 2014, Genome alignment with graph data structures: a comparison, BMC Bioinformatics 15:99.
Kent, 2002, BLAT-The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Koolen, 2008, Clinical and Molecular Delineation of the 17q21.31 Microdeletion Syndrome, J Med Gen 45(11):710-720.
Kumar, 2010, Comparing de novo assemblers for 454 transcriptome data, BMC Genomics 11:571.
Kurtz, 2004, Versatile and open software for comparing large genomes, Genome Biol 5:R12.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Larkin, 2007, Clustal W and Clustal X version 2.0, Bioinformatics 23(21):2947-2948.
Lecca, 2015, Defining order and timing of mutations during cancer progression: the TO-DAG probabilistic graphical model, Frontiers in Genetics, vol. 6 Article 309 1-17.
Lee et al. Accurate read mapping using a graph-based human pan-genome. (May 2015) American Society of Human Genetics 64th Annual Meeting Platform Abstracts; Abstract 41.
Lee, 2002, Multiple sequence alignment using partial order graphs, Bioinformatics 18(3):452-464.
Lee, 2003, Generating consensus sequences from partial order multiple sequence alignment graphs, Bioinformatics 19(8):999-1008.
Lee, 2005, Bioinformatics analysis of alternative splicing, Brief Bioinf 6(1):23-33.
Lee, 2014, Accurate read mapping using a graph-based human pan-genome, ASHG 2014 Abstracts.
LeGault, 2010, Learning Probalistic Splice Graphs from RNA-Seq data, pages.cs.wisc.edu/~legault/cs760_writeup.pdf retrieved from the internet on Apr. 6, 2014.
LeGault, 2013, Inference of alternative splicing from RNA-Seq data with probabilistic splice graphs, Bioinformatics 29(18):2300-2310.
Leipzig, 2004, The alternative splicing gallery (ASG): Bridging the gap between genome and transcriptome, Nuc Acids Res 23(13):3977-3983.
Li, 2009, Fast and accurate short read alignment with Burrows-Wheeler Transform. Bioinformatics 25:1754-60.
Li, 2010, A survey of sequence alignment algorithms for next-generation sequencing, Briefings in Bionformatics 11(5):473-483.
Lipman, 1985, Rapid and sensitive protein similarity searches, Science 227(4693):1435-41.
Lucking, 2011, PICS-Ord: unlimited coding of ambiguous regions by pairwise identity and cost scores ordination, BMC Bioinf 12:10.

* cited by examiner

DATA SECURITY IN BIOINFORMATIC SEQUENCE ANALYSIS

CROSS-REFERENCE TO RELATED APPLICATION

This application claims priority to and the benefit of, and incorporates herein by reference in its entirety, U.S. Provisional Patent Application No. 62/465,459, filed on Mar. 1, 2017.

TECHNICAL FIELD

Embodiments of the present invention relate generally to workflow processing of bioinformatic data, e.g., data obtained by sequencing a nucleic acid.

BACKGROUND

The science of bioinformatics applies sophisticated analytic techniques to biological data, such as genome sequences, to better understand the underlying biology. "Next generation" sequencing systems perform chemical analysis of a sample containing nucleic acid and generate many sequence "reads," i.e., short nucleic-add segments typically less than 1000 base pairs (bp) in length. Overlapping reads are aligned to a reference sequence (such as a genome) to reveal important genetic or structural information (e.g., biomarkers for disease). Ultimately, the goal of sequence alignment is to combine the set of nucleic acid reads produced by the sequencer to achieve a longer read (a "contig") or even the entire genome of the sample source. Because the sequence data from next-generation sequencers often comprises millions of shorter sequences that together represent the totality of the target sequence, aligning the reads is complex and computationally expensive. Systems that perform this type of alignment may represent sequences as graph data structures (e.g., directed acyclic graphs); a representative system is described in U.S. Pat. No. 9,390,226, the entire disclosure of which is hereby incorporated by reference.

The graph-based references may be quite valuable, representing the results of multiple sequencing efforts that have been analyzed to identify variants—e.g., single-nucleotide polymorphisms (SNPs), structural variants, insertions and deletions—among different individuals of the same species. Candidate sequences, which may be very short "k-mers" (sequences of length k bp, where k is generally less than 100 and often less than 20) or longer reads, are analyzed against a reference sequence using an alignment tool, which determines the degree of similarity between the candidate sequence and the reference sequence over the entirety of the latter—that is, the alignment tool finds the best match between an input segment and the reference segment wherever this match occurs and reports a score indicating the quality of the match.

Although service bureaus that accept candidate sequences and perform alignments against proprietary reference sequences can easily maintain their physical security, these sequences nonetheless remain vulnerable to illicit reconstruction by intruders who may, for example, submit candidate sequences structured so that the resulting alignment provides information about the reference sequence graph. In sufficient quantity, such information can permit reconstruction or all or part of the graph. Detecting malicious input represents a considerable challenge in automated, cloud-based service environments that massively accept candidate sequences from often-anonymous sources.

SUMMARY

In various embodiments, the invention pertains to systems and methods for protecting information stored in private references that are available to be queried—e.g., graph-based sequence references that users query through an interface, providing short reads to obtain the results of an alignment against the reference sequence. Before returning results to a user, and in some cases before performing the alignment, the query and/or alignment results are analyzed to determine whether the query represents an attack.

Accordingly, in a first aspect, the present invention pertains to a system for identifying alignments between a received biological sequence and a stored reference biological sequence without compromising the reference sequence. In various embodiments, the system comprises a first memory partition for storing a reference sequence corresponding to a nucleic acid; a second memory partition for storing one or more received comparison sequences corresponding to a nucleic acid; an alignment module for identifying at least one alignment between each comparison sequence and the reference sequence; a communication module for receiving the comparison sequence(s) and transmitting an alignment generated by the alignment module; and a security module, executable by the processor. The security module may (i) analyze at least one comparison sequence for the presence of sequence anomalies associated with malicious activity enabled by alignment of the one or more comparison sequences with the reference sequence, and rejecting the one or more comparison sequences if a sequence anomaly is detected, or (ii) analyze the at least one alignment for post-alignment anomalies associated with malicious activity and preventing transmission of the alignment if a post-alignment anomaly is detected, or (iii) perform both (i) and (ii).

In some embodiments, the reference sequence is stored in the first memory partition as a graph. Sequence anomalies may be indicative of inauthentic sequence data, and malicious activity may involve reconstruction of at least a portion of the reference sequence. In various embodiments, the security module is configured to (i) determine the distribution of genomic features in the comparison sequence and (ii) prevent alignment of the comparison sequence to the reference sequence if the distribution deviates by a predetermined threshold. Genomic features may correspond to nucleic acid base pair frequency and/or sequencing base quality values.

The system may feature a database containing a plurality of k-mer distribution statistics. In these embodiments, the security module may be configured to (i) generate one or more sets of k-mers from the one or more comparison sequences and (ii) calculate distribution statistics on the one or more sets of k-mers and (iii) reject the one or more comparison sequences if the statistics computed therefrom deviate from corresponding statistics in the database by greater than a predetermined threshold. The security module may also detect variants, and the system may include a database containing a disease variant dataset comprising genomic variants associated with one or more diseases; in these embodiments, the security module may be configured to determine a frequency with which disease variants occur in the detected variants. For example, the security module may prevent transmission of the alignment if the frequency with which disease variants occur in the detected variants is above a predetermined threshold.

In some embodiments, the system features a database containing a plurality of nucleic-acid sequences. In such embodiments, the security module may be configured to (i) determine whether any of the database entries occurs in the one or more comparison sequences and (ii) if so, reject the one or more comparison sequences. Nucleic-acid sequences in the dataset may have lengths less than 20 and/or may correspond to lethal alleles or portions thereof, or to a plurality of genetic diseases.

The security module may, for example, implement a classifier to determine whether the nucleic-acid sequences deviate from the comparison sequences in the database by more than the predetermined threshold. For example, the security module may computationally implement a neural network.

In another aspect, the invention relates to a method of aligning a received biological sequence and a stored biological reference sequence without compromising the reference sequence. In various embodiments, the method comprises receiving one or more comparison sequences corresponding to a nucleic acid; analyzing each comparison sequence for the presence of sequence anomalies associated with malicious activity enabled by alignment of the one or more comparison sequences with a reference sequence; and rejecting the one or more comparison sequences if a sequence anomaly is detected.

In some embodiments, the method further includes aligning the one or more sequences against the reference sequence; analyzing the alignment(s) for post-alignment anomalies associated with malicious activity; and preventing transmission of the alignment if a post-alignment anomaly is detected. The method may, in various embodiments, include the steps of computing linkage disequilibrium statistics associated with the one or more received comparison sequences; comparing the computed linkage disequilibrium statistics with corresponding linkage disequilibrium statistics associated with loci of the reference sequence; and rejecting the one or more comparison sequences if the computed linkage disequilibrium statistics computed therefrom deviate from the corresponding linkage disequilibrium statistics by greater than a predetermined threshold.

In some embodiments, the method includes implementing a classifier (e.g., a neural network) to determine whether the linkage disequilibrium statistics deviate from the comparison sequences in the database by more than a predetermined threshold.

In various embodiments, the method includes calculating variant distribution statistics from the one or more comparison sequences; comparing the variant distribution statistics against a database of normal variant distribution statistics; and rejecting the comparison sequence(s) if the calculated variant distribution sequences deviate from the normal variant distribution statistics by greater than a predetermined threshold. For example, the variant distribution statistics may correspond to a group comprising single nucleotide polymorphisms, insertions of varying lengths, and deletions of varying lengths.

The term "substantially" or "approximately" means ±10% (e.g., by weight or by volume), and in some embodiments, ±5%. The term "consists essentially of" means excluding other materials that contribute to function, unless otherwise defined herein. Nonetheless, such other materials may be present, collectively or individually, in trace amounts. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing will be more readily understood from the following detailed description of the invention, in particular, when taken in conjunction with the drawings, in which.

DETAILED DESCRIPTION

Representative Architecture

Figure 1:
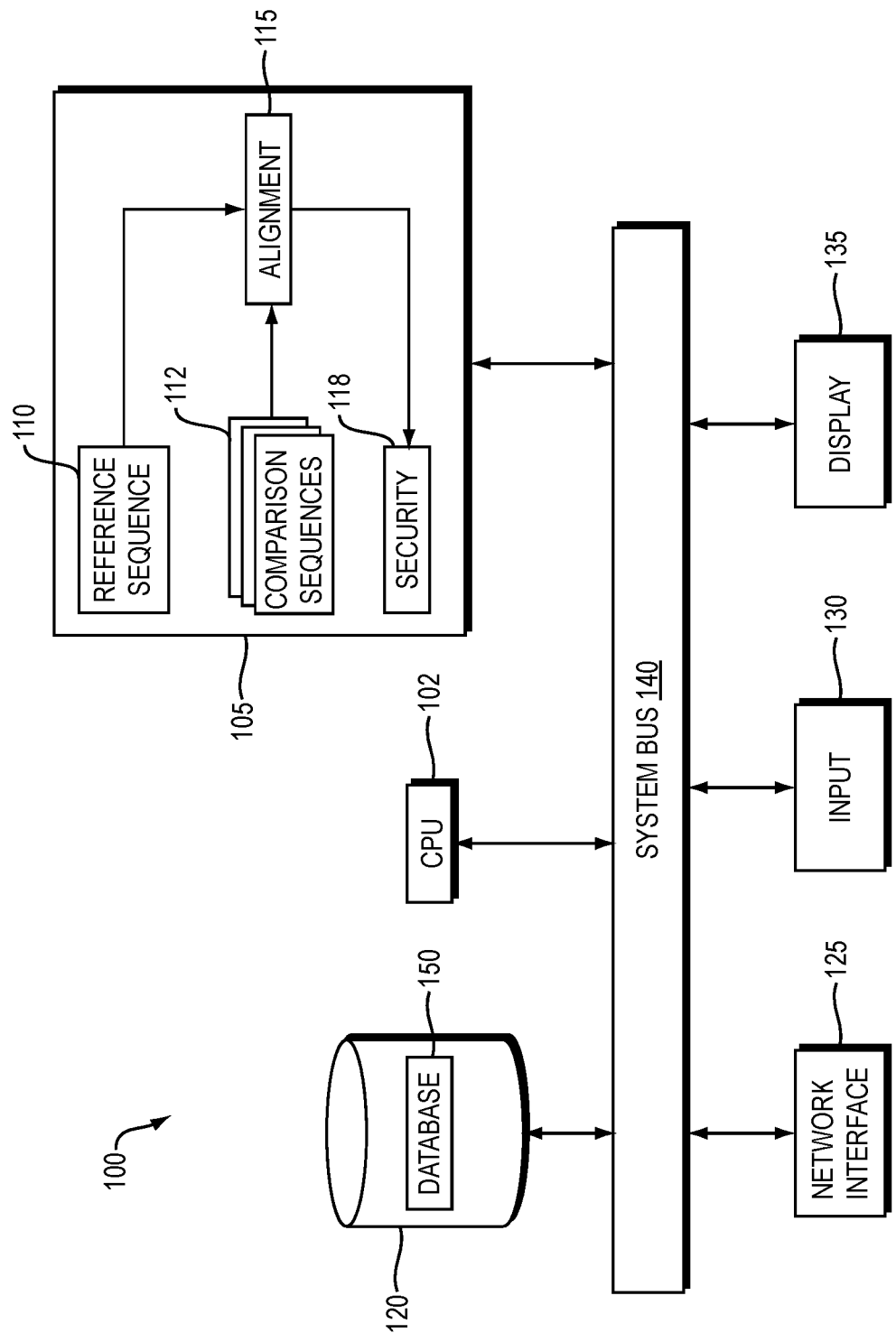
FIG. 1 is a block diagram of a representative computational architecture for implementing embodiments of the present invention.

The general approach taken by embodiments of the present invention is illustrated in FIG. 1, which illustrates, in block-diagram form, an exemplary computer 100 with features enabling it to align a received biological sequence and a stored biological reference sequence without compromising the reference sequence. The operation of computer 100 is directed by a central-processing unit ("CPU") 102. A main system memory 105, generally implemented as a bank of random-access memory (RAM), includes partitions for storing a nucleic-acid reference sequence 110, one or more received comparison sequences 112 each corresponding to a nucleic acid, an alignment module 115 for identifying alignments between each comparison sequence and the reference sequence, and a security module 118. As described in greater detail below, security module 118 may perform one or more security analyses to detect malicious activity. For example, security module 118 may analyze comparison sequences for the presence of sequence anomalies associated with malicious activity enabled by alignments with the reference sequence; security module 118 rejects comparison sequences if a sequence anomaly is detected. Alternatively or in addition, security module 118 may analyze alignments for post-alignment anomalies associated with malicious activity, and may prevent transmission of the alignment if a post-alignment anomaly is detected.

More generally, main memory 105 contains instructions that control the operation of CPU 102 and its interaction with other hardware components. An operating system directs the execution of low-level, basic system functions such as memory allocation, file management and operation of one or more mass storage devices 120, typically one or more nonvolatile disk drives. A network interface 125 facilitates interaction with other computers and resources, permitting system 100 to receive comparison sequences and transmit alignments to customers. The computer 100 also includes input devices 130 (e.g., a keyboard, a mouse or other position-sensing device, etc.), by means of which a user can interact with the system, and a screen display 135. The computer 100 further includes a bidirectional system bus 140 over which the system components communicate, and as described in greater detail below, mass-storage device 120 may include one or more databases 150.

The distribution of functionality shown in FIG. 1 is representative only and intended to provide one possible topology. It is possible to distribute the functionality illustrated in FIG. 1 among more or fewer computational entities as desired, and components may intercommunicate over a computer network, e.g., a wired or wireless local-area network (LAN), wide-area network (WAN) and/or other types of networks. When used in a LAN networking environment, components may be connected to the LAN through a network interface or adapter. When used in a WAN networking environment, components typically include a modem or other communication mechanism. Modems may be internal or external, and may be connected to the system bus via the user-input interface, or other appropriate mechanism. Computers may be connected to the Internet, an Intranet, Extranet, Ethernet, or any other system that provides communications. Some suitable communications protocols may include TCP/IP, UDP, or OSI, for example. For wireless communications, communications protocols may include the cellular telecommunications infrastructure, WiFi or other 802.11 protocol, Bluetooth, Zigbee, IrDa or other suitable protocol. Furthermore, components of the system may communicate through a combination of wired or wireless paths.

Figure 2:
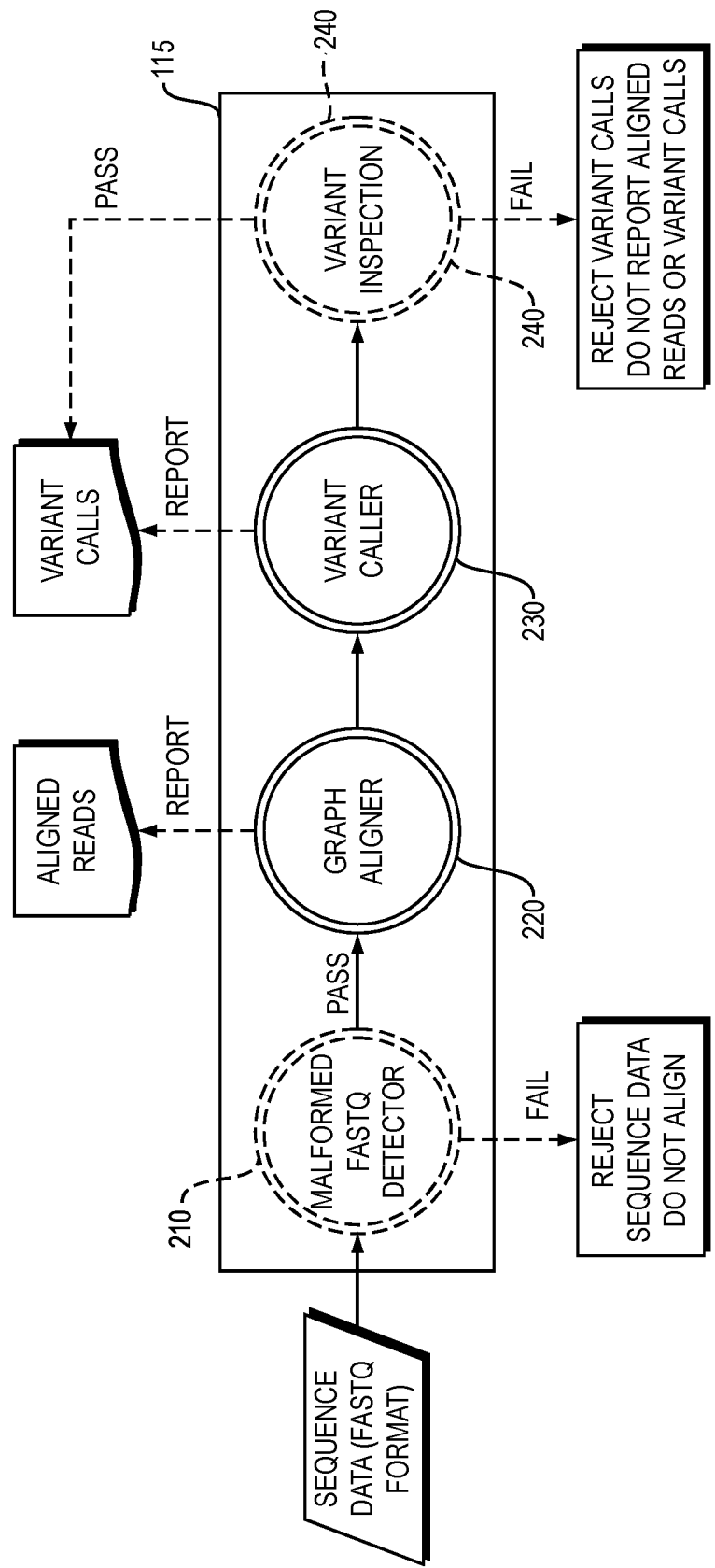
FIG. 2 is a block diagram showing in greater detail elements of a representative embodiment of the invention.

Components of a representative alignment module 115 are shown in FIG. 2. The alignment module 115 accepts input sequence data in, for example, FastQ format. An optional preprocessing module 210 analyzes input sequences for anomalies in the data itself that are indicative of an attack, or which in any event should not be processed due to intrinsic errors or malformation. A graph aligner 220 (as described, for example, in the '226 patent) aligns reads to the graph reference genome and reports back the mapped position and quality scores indicating the degree of alignment between a received candidate sequence and the reference sequence.

A variant caller 230 identifies variants (e.g., single-nucleotide polymorphisms, structural variants, insertions and deletions) or "polymorphisms." That is, after the alignment module 220 maps the input reads to the reference sequence (e.g., a genome), the variant caller 230 identifies variant sites and assigns a genotype to the reads. The variants typically represent mutations that an organism inherits biologically from its parents. Variant callers, which are well-known in the art, generally employ statistical or heuristic algorithms to predict the likelihood of variation at each position in the aligned reads. See, e.g., Liu et at, "Variant Callers for Next-Generation Sequencing Data: A Comparison Study," *PloS One*, 2013:8(9), e75619, the entire disclosure of which is hereby incorporated by reference. A variant inspection module 240 analyzes the resulting alignments, reflecting identified variants, for anomalies associated with malicious activity.

Following the analysis, if no evidence of an attack is detected, the results produced by alignment module 115 are transmitted to the requester in the form of a report via network interface 125. The report typically includes the aligned reads and the called variants.

Those skilled in the art will appreciate that the invention may be practiced with various computer system configurations, including multiprocessor systems, microprocessor-based or programmable consumer electronics, minicomputers, mainframe computers, and the like. The invention may also be practiced in distributed computing environments where tasks are performed by distributed processing devices linked through a communications network. In a distributed computing environment, program modules may be located in both local and remote computer-storage media including memory storage devices.

Any suitable programming language may be used to implement without undue experimentation the modules described herein and the analytical functions described below. Illustratively, the programming language used may include assembly language, Ada, APL, Basic, C, C++, C*, COBOL, dBase, Forth, FORTRAN, Java, Modula-2, Pascal, Prolog, Python, REXX, and/or JavaScript for example. Further, it is not necessary that a single type of instruction or programming language be utilized in conjunction with the operation of the system and method of the invention. Rather, any number of different programming languages may be utilized as is necessary or desirable.

CPU 102 may be a general-purpose processor, but may instead be or utilize any of a wide variety of other technologies including special-purpose hardware, a microcomputer, mini-computer, mainframe computer, programmed microprocessor, micro-controller, peripheral integrated circuit element, a CSIC (customer-specific integrated circuit), ASIC (application-specific integrated circuit), a logic circuit, a digital signal processor, a programmable logic device such as an FPGA (field-programmable gate array), PLD (programmable logic device), PLA (programmable logic array), smart chip, or any other device or arrangement of devices that is capable of implementing the functions of the invention as herein described.

Preprocessing Module 210

Preprocessing module 210 executes one or more analyses on one or more of a set of input sequences to detect anomalies. These may be errors of form that preclude generation of proper alignments, but more importantly, module 210 scans for patterns indicative of a malicious attack. In particular, module 210 looks for suspicious k-mers in the reads, deviations in k-mer density and frequency, or other metrics to compare against reference data, such as GC content (see, e.g., Li, "G+C Content Evolution in the Human Genome," *eLS* (April 2013), the entire disclosure of which is hereby incorporated by reference), and base quality distribution. Only if preprocessing module 210 detects no anomalies indicative of an attack are the reads aligned and variants called.

In one embodiment, preprocessing module 210 exploits knowledge regarding loss of genetic function. Specifically, recent work suggests that certain genes never undergo mutation that results in loss of function in viable humans, i.e., negation of the biological role played by the protein that the gene encodes. Mutant alleles that cause the death of the organism that carries them are known as "lethal alleles" (which may be dominant or recessive, and include genes relating to early muscular and skeletal development). In some instances, lethal alleles are "embryonic lethal" (i.e., resulting in death during the embryonic stage of development). An example of an embryonic lethal genotype is a homozygous mutation at nucleotide 1138 in FGFR3; whereas individuals with one copy of the mutated allele survive with a condition known as achondroplasia, those with two copies of the allele do not survive past the fetal stage. In other instances, lethal alleles shorten the lifespan of an organism (e.g., the expanded repeat Huntingtin allele found on human chromosome 4, which leads to Huntington's disease). Mutations that are chemically permissible (i.e., consistent with nucleic-acid structure and chemical composition) but which do not occur in nature (or occur in nature at an extremely low frequency) represent indicators of potentially inauthentic data. Moreover, these impossible sequences are more likely than others to be generated by a system for producing fraudulent data for use in an attack. Such a system might, for example, automatically generate standard types of mutations in each of a large set of important genes. Preprocessing module 210 may, therefore, scan the input reads for the presence of telltale k-mers indicative of such data.

One or more sets of target k-mers may be generated as follows. First, one or more genes that do not admit loss-of-function mutations are identified. Next, a set of a priori plausible mutations in those genes that are not present in any viable organismic (e.g., human) genomes that have been studied is generated in accordance with established mutation patterns. A set of k-mers (e.g., for k=12) appearing in sequences representing those mutations and not appearing in standard human genome references is then generated. These k-mers ideally span the space of possible variations that might appear in read sequences that align with the identified genes. Scanning of the input reads for those k-mers may be performed in time that is linear with respect to the size of the input, after conventional preprocessing. A set of reads containing one or more target k-mers may be rejected; the more such k-mers that are present in a candidate set of reads, the more likely it is that they represent a malicious attack. The number of target k-mers that must be present for a set of candidate reads to be rejected may be determined by those of skill in the art without undue experimentation based on the tolerance for risk, the number of detected k-mers relative to the number of reads submitted, etc. Similar considerations apply across all strategies discussed herein.

In some cases, the mere presence of a sufficient number of variants (and therefore diseases) may be indicative of an attack, and these may be identified by scanning the sequence reads for associated (legitimate) k-risers. Identifying the presence of k-mers in sequence data may be accomplished in a computationally tractable fashion using, for example, "fast genotyping." See, e.g., Shajii et al., "Fast genotyping of known SNPs through approximate k-mer matching," *Bioinformatics*, 2016 Sep. 1; 32(17):i538-i544, the entire disclosure of which is hereby incorporated by reference. That is, instead of analyzing the called variants post-alignment, the presence of multiple k-mers indicates the presence of variants (and therefore, diseases, or the presence of lethal alleles) may be inferred from an initial scan of the sequence reads.

Identifying sequence anomalies in sequence data prior to alignment is beneficial because it can reduce the amount of time (and therefore, computational cost) associated with performing sequence read alignment on a potentially malicious dataset. Datasets determined to be malicious are rejected prior to sequence alignment, which typically represents the majority of the cost associated with a whole genome sequencing and analysis workflow. However, because no full alignment has been performed these techniques may suffer from false negatives. Alternatively, to improve results, these detection strategies may be implemented post-alignment by variant-inspection module 240, described in greater detail below. For example, module 240 may analyze the variant calls for mutations that fall within loss-of-function genes, and identify as anomalous those that result in a nonsynonymous substitution. For example, module 240 may apply a mask to an alignment for just those genes.

In some embodiments, modules 210 and 240 are both used to identify sequence anomalies associated with malicious data in an incoming data set. However, in some embodiments, only the preprocessing module 210 or the variant-inspection module 240 are used.

Figure 3A:
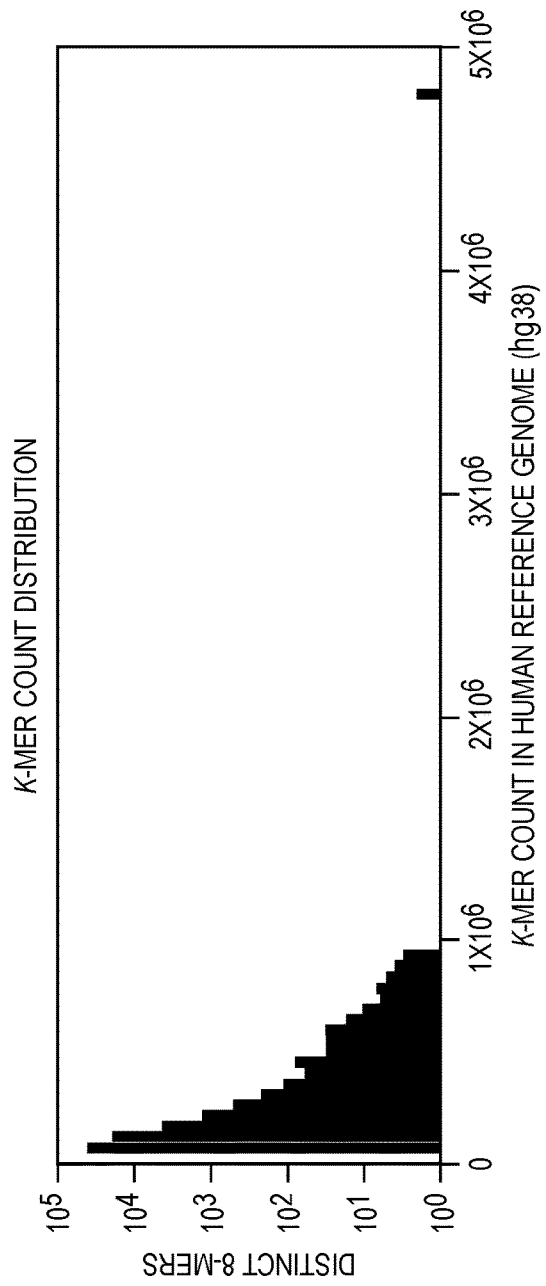
FIG. 3 graphically illustrates k-mer frequency distributions in a human reference genome.
Figure 3B:
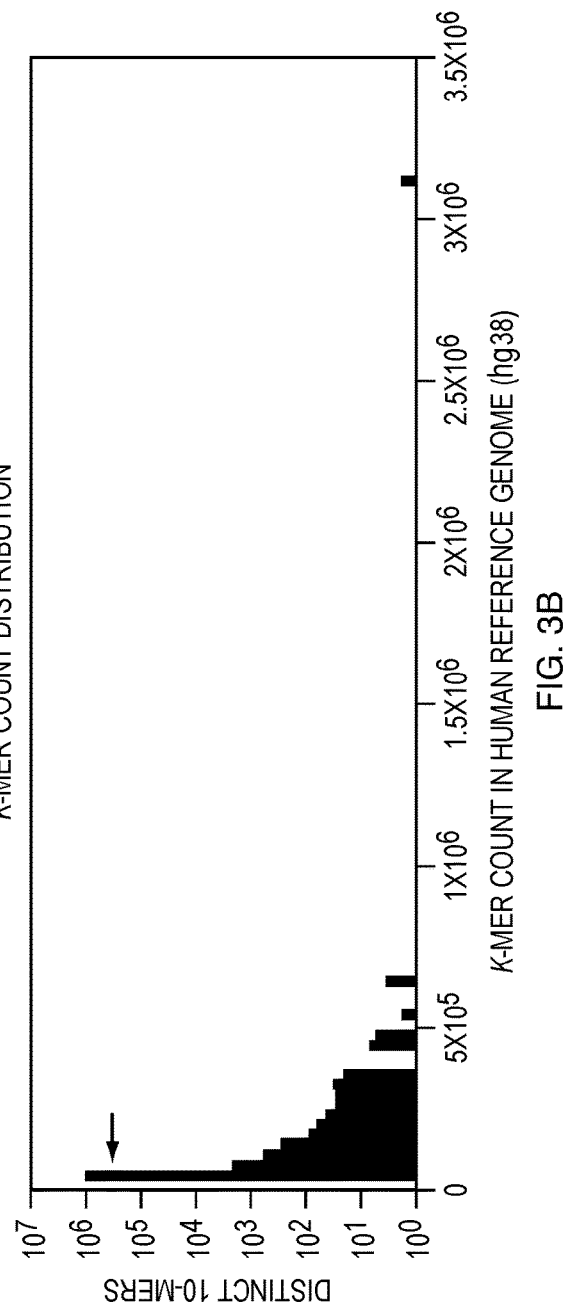

Another analysis that may be performed on input reads is testing for the expected frequency (i.e., distribution) of k-mers therein. Representative k-mer frequency distributions are shown in FIG. 3. First, the frequency of distinct k-mers of a given length in the organismic genome (or a "normal" sequence read sample) is established and stored, e.g., in a reference database 150 (see FIG. 1). For k-mers of length 8-14 base pairs, for example, the frequency of distinct k-mer distributions is expected to follow a power-law distribution. The number of unique k-mers in the genome increases with k-mer length. The k-mer distribution in the incoming sequence reads is obtained and compared with the expected distribution, with deviations of sufficient magnitude flagged as inauthentic. One computational approach is to normalize the set of k-mer frequencies to sum to one, and then calculate information divergence between the two sets. This may be represented as Kullback-Leibler divergence, or alternatively, a Kolmogorov-Smirnov (K-S) test may be used to compare the distribution of sample pairs. In addition, preprocessing module 210 may flag reads as inauthentic if their associated k-mer distribution plot lacks the peak of abundant k-mers that correspond to Alu elements. An advantage to this k-mer based approach is that it also will identify datasets that are malformed innocently. Privacy concerns are also reduced because it does not require analysis of the diseases that may be associated with a sample. It will also identify "white noise attacks" or randomized k-mers sent to the aligner to obtain all possible variations in a graph.

Variant-Inspection Module 240

Variant-inspection module 240 may implement one or more of various strategies for identifying variants indicative of an attack.

a. Disease Frequencies

A reference sequence may be attacked with data "spiked" with the genetic profiles of various diseases. In one strategy, module 240 determines the degree to which one or more specific diseases is represented in a set of input data. This may be accomplished by (a) determining a set of important diseases; (b) determining, for each of those diseases, one or more variants (e.g., SNPs) characteristic of the disease; (c) aggregating these variants into a reference set; and (d) for a given set of input data, determining the frequency with which each variant in the dataset occurs in that data. For example, module 240 may detect the presence of SNPs associated with multiple known diseases, and which are highly unlikely to occur in a single sample. The greater the likelihood of non-occurrence, the higher is the likelihood that the input reads represent an attack. In some embodiments, disease information may be stored as metadata associated with nodes or edges of the reference graph.

b. Properties of the Input Dataset

Some types of fraudulent data used in attacks differ in detectable ways from legitimate datasets. For example, they may include more mutations than real data or the mutations may be distributed unnaturally. The short reads constituting an input set may be put into graph form and analyzed computationally for patterns indicative of an attack. For example, a graph (e.g., a directed acyclic graph, or DAG)

may be generated to represent multiple (e.g., 1000) genomes and, if desired, other sources of legitimate data. One or more graph metrics, such as average vertex connectivity and average closeness centrality, are generated for this graph. These represent benchmark metrics. For any given input dataset, a graph representing that data set is similarly generated, and the same metrics) are computed for the input dataset graph. These metrics are compared with the benchmark metrics; and sufficient deviation therefrom indicates that the reads likely represent an attack.

Analysis of graph metrics may involve more than simple numeric comparison. For example, there may be several metrics and many submitted reads. Although it is possible to compute averages of the read metrics or a statistical property such as standard deviation, these quantities may be too coarse; for example, the attack may be focused on a subset of submitted reads precisely in order to camouflage them in a large dataset. Accordingly, the computed metrics may be used as inputs to a machine-learning or data-analysis technique such as logistic regression (with an appropriate threshold) or a neural network trained to distinguish innocent patterns from those indicating an attack. Such techniques are well-known and are straightforwardly implemented without undue experimentation.

c. Linkage Disequilibrium

Variant-inspection module 240 may also exploit linkage disequilibrium, i.e., the non-random association of alleles at different genome positions. Genome loci are said to be in linkage disequilibrium (LD) when the frequency of association of their different alleles is higher or lower than what would be expected if they were independent and associated randomly. It is difficult to construct fraudulent data that is both useful for attacking purposes and also faithful to established patterns. Thus, a library of LD statistics involving loci of likely interest to attackers may be created. Following variant calling on a given set of input data, allele frequencies and LD are computed for that data set. These are compared, either directly or using a machine-learning or data-analysis technique as discussed above, to detect levels or patterns indicative of an attack.

d. Variant Count and Density

Typically, a given human genome should only have 3-4 million SNPs called. Inauthentic data supplied by an attacker might lead to many more called SNPs, as the objective may be to identify all or most of the variants present in the graph. Accordingly, another way to identify inauthentic data is to assess whether the number of called variants significantly deviates from the expected number, e.g., in excess of 6-10 million.

Attackers might get around this by performing multiple runs and confining the inauthentic data to smaller regions or segments of the genome. This may be detected by analyzing variant density. If the variant density in a given region of the genome exceeds an expected amount (e.g., most people exhibit 1 SNP about every 1000 bp), the results may be rejected before variant calling. Similarly, the variant sets themselves may be analyzed for other properties, such as the distribution of insertion or deletion lengths, which typically follow a power law. See, e.g., Cartwright, "Problems and Solutions for Estimating Indel Rates and Length Distributions," *Mol. Biol. Evol.* 26(2):473-480 (2009), the entire disclosure of which is hereby incorporated by reference.

Representative Methods

Figure 4:
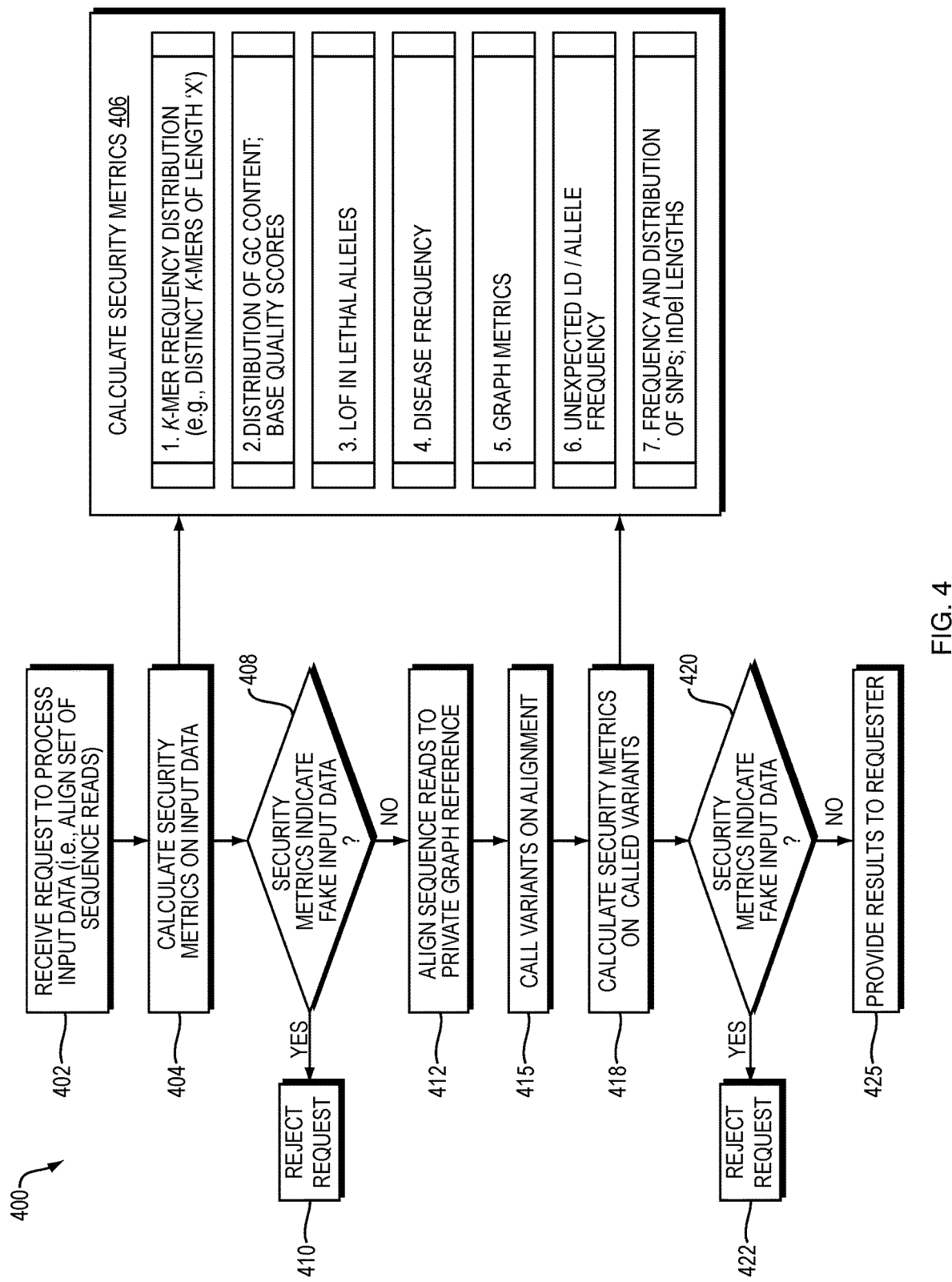
FIGS. 4-6 are flow charts illustrating, respectively, techniques for pre- and post-alignment analysis, training, and classification in accordance with embodiments of the invention.

A representative technique 400 for pre- and post-alignment analysis is shown in FIG. 4. In a first step 402, input data (e.g., a set of sequence reads) is received with a request for processing. Next, security metrics are computed on the input data (steps 404, 406). As described above, these metrics may include one or more of k-mer frequency distribution, GC content distribution, base quality scores, tests for loss of function in lethal alleles, disease frequency, graph metrics, examination of LD patterns and allele frequencies, analysis of SNP frequency and distribution, and analysis of the distribution of insertion or deletion lengths.

If the computed security metrics are indicative of fraudulent input data (step 408), the request is rejected (step 410). Otherwise, the received sequence reads are aligned against the proprietary graph (step 412), variant calling is performed (step 415), and a second layer of security is invoked with security metrics computed on called variants (step 418). Once again, if the security metrics indicate fraudulent input data (step 420), the request is rejected (step 422), otherwise results are provided to the requester (step 425).

Figure 5:
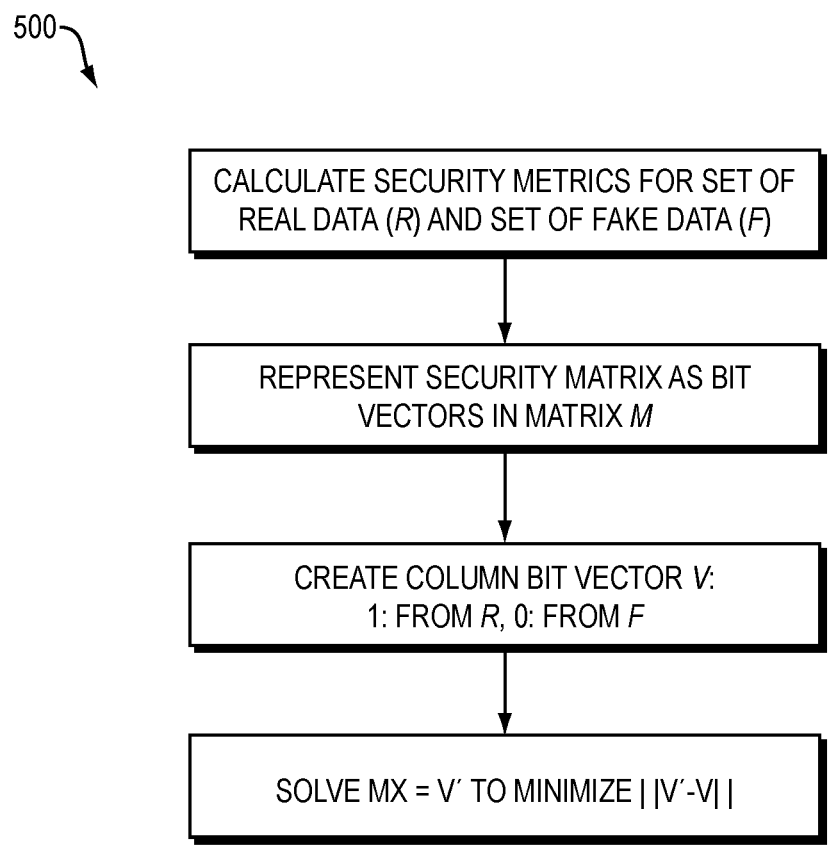
Figure 6:
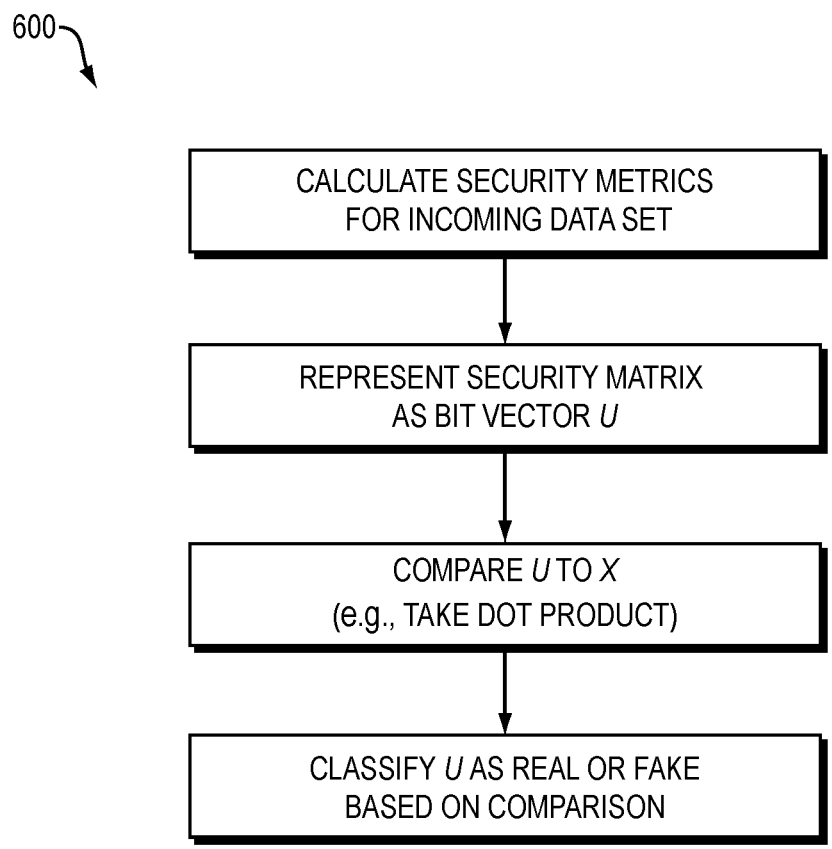

Representative techniques for training a machine-learning system and using it to classify legitimate and anomalous cases are illustrated in FIGS. 5 and 6, respectively. It should be understood, however, that machine learning and data-analytic techniques may be used in connection with any of the analyses and metrics described above. For example, variant counts, k-mer density, SNPs for multiple diseases, etc. may be used as features for a classifier. Other features of the sequence reads, such GC content and base quality distribution, may be used alternatively or in addition to increase the predictive capability of the learning technique and improve its accuracy. So long as the classifier is trained on a "normal" sample, then even features not directly associated with inauthentic data may nonetheless have predictive value.

With reference to FIG. 5, a representative training sequence 500 proceeds as follows.

(1) Collect a diverse collection of real data sets (call it R).

(2) Create a set of fraudulent data sets (e.g., by spiking real data with variants indicating disease). (Call it F.)

(3) Perform SNP frequency analysis, as described above, on each data set in R and in F; this will produce two sets of vectors of SNP frequencies (one set of frequencies in which the members correspond to data sets in R and one in which the members correspond to data sets in F).

(4) Perform loss-of-function analysis on each data set in R and in F; this will produce two sets of k-mer "hit frequencies" (the frequencies with which they correspond to k-mers in lethal alleles). One of these sets will contain values corresponding to data sets in R, and one will contain values corresponding to data sets in F. In theory, it is natural to use vectors of hit frequencies for each data set rather than single variables; this facilitates separation of information about hit rates for different parts of the k-mer library. In practice, however, this creates many extra variables, and aggregating this information is computationally easier and does not compromise the results.

(5) Test for properties of the input dataset as described above on each data set in R and in F; this will produce two sets of vectors of metrics (one set of metrics in which the members correspond to data sets in R and one in which the members correspond to data sets in F). For concreteness, one can suppose that these vectors are of length two and that the first element of each vector corresponds to the graph's average vertex connectivity and that the second element of each vector corresponds to the graph's average closeness centrality.

(6) Perform LD analysis on each data set in R and in F; this will produce two sets of vectors of LD values (one set of values in which the members correspond to data sets in R and one in which the members correspond to data sets in F).

(7) Aggregate the values and vectors in (3) and (4) into a single matrix in which each row corresponds to an element of R or of F. Each column corresponds to a position in the vectors from (3), (5), and (6) or to the frequencies determined in (6). These rows, that is, can be viewed as concatenations of all the values determined in steps (3)-(6). Call this matrix M.

(8) Create a column vector of ones and zeroes, with ones corresponding to rows of data generated from real data and zeroes corresponding to rows of data generated from fake data. Call this vector V.

(9) Solve the equation MX=V' in X so as to minimize $\|V'-V\|$; that is, find a column vector X that, when multiplied on the left by M, gives values that are closest to V in the sense of minimizing the squared error.

With reference to FIG. 6, for any incoming data set, perform steps (3)-(6) on that set to generate the analogous row vector U. Take its dot product with X as determined in (9), which will yield a number corresponding to a prediction whether the data is real or fake (ideally, numbers corresponding to real data will be near 1 and those corresponding to fake data will be near 0). One can use a threshold (e.g., 0.5) to determine whether to classify the data as real or fake.

While particular embodiments of the invention have been illustrated and described in detail herein, it should be understood that various changes and modifications might be made to the invention without departing from the scope and intent of the invention. From the foregoing it will be seen that this invention is one well adapted to attain all the ends and objects set forth above, together with other advantages, which are obvious and inherent to the system and method. It will be understood that certain features and sub-combinations are of utility and may be employed without reference to other features and sub-combinations. This is contemplated and within the scope of the appended claims.

The invention claimed is:

1. A system for identifying alignments between a received biological sequence and a stored reference biological sequence without compromising the reference sequence, the system comprising:
   a first memory partition for storing a reference sequence corresponding to a nucleic acid;
   a second memory partition for storing one or more received comparison sequences corresponding to a nucleic acid;
   an alignment module for identifying at least one alignment between each comparison sequence and the reference sequence;
   a communication module for receiving the one or more comparison sequences and transmitting an alignment generated by the alignment module; and
   a security module, executable by the processor, for (i) analyzing at least one comparison sequence for the presence of sequence anomalies associated with malicious activity enabled by alignment of the one or more comparison sequences with the reference sequence, and rejecting the one or more comparison sequences if a sequence anomaly is detected, or (ii) analyzing the at least one alignment for post-alignment anomalies associated with malicious activity and preventing transmission of the alignment if a post-alignment anomaly is detected, or (iii) performing both (i) and (ii),
   wherein (a) the security module also detects variants, and further comprising a database containing a disease variant dataset comprising genomic variants associated with one or more diseases, the security module being configured to determine a frequency with which disease variants occur in the detected variants, and (b) the security module prevents transmission of the alignment if the frequency with which disease variants occur in the detected variants is above a predetermined threshold.

2. The system of claim 1, wherein the reference sequence is stored in the first memory partition as a graph.

3. The system of claim 1, wherein the sequence anomalies are indicative of inauthentic sequence data.

4. The system of claim 1, wherein the malicious activity is reconstruction of at least a portion of the reference sequence.

5. The system of claim 1, wherein the security module is configured to (i) determine a distribution of genomic features in the comparison sequence and (ii) prevent alignment of the one or more comparison sequences to the reference sequence if the distribution deviates by a predetermined threshold.

6. The system of claim 5, wherein the genomic features correspond to nucleic acid base pair frequency or sequencing base quality values.

7. The system of claim 1, further comprising a database containing a plurality of k-mer distribution statistics, the security module being configured to (i) generate one or more sets of k-mers from the one or more comparison sequences and (ii) calculate distribution statistics on the one or more sets of k-mers and (iii) reject the one or more comparison sequences if the statistics computed therefrom deviate from corresponding statistics in the database by greater than a predetermined threshold.

8. The system of claim 1, further comprising a database containing a plurality of nucleic-acid sequences, the security module being configured to (i) determine whether any of the database entries occurs in the one or more comparison sequences and (ii) if so, reject the one or more comparison sequences.

9. The system of claim 8, wherein the nucleic-acid sequences in the dataset have lengths less than 20.

10. The system of claim 8, wherein the nucleic-acid sequences correspond to lethal alleles or portions thereof.

11. The system of claim 8, wherein the nucleic-acid sequences correspond to a plurality of genetic diseases.

12. The system of claim 8, wherein the security module implements a classifier to determine whether the nucleic-acid sequences deviate from the comparison sequences in the database by more than the predetermined threshold.

13. A method of aligning a received biological sequence and a stored biological reference sequence without compromising the reference sequence, the method comprising:
   receiving one or more comparison sequences corresponding to a nucleic acid;
   analyzing each comparison sequence for the presence of sequence anomalies associated with malicious activity enabled by alignment of the one or more comparison sequences with a reference sequence;
   calculating variant distribution statistics from the one or more comparison sequences;
   comparing the variant distribution statistics against a database of normal variant distribution statistics; and
   rejecting the one or more comparison sequences if (a) a sequence anomaly is detected or (b) the calculated variant distribution sequences deviate from the normal variant distribution statistics by greater than a predetermined threshold.

14. The method of claim 13, further comprising:
   aligning the one or more sequences against the reference sequence;

analyzing the at least one alignment for post-alignment anomalies associated with malicious activity; and preventing transmission of the alignment if a post-alignment anomaly is detected.

15. The method of claim 13, further comprising:

computing linkage disequilibrium statistics associated with the one or more received comparison sequences;

comparing the computed linkage disequilibrium statistics with corresponding linkage disequilibrium statistics associated with loci of the reference sequence; and rejecting the one or more comparison sequences if the computed linkage disequilibrium statistics computed therefrom deviate from the corresponding linkage disequilibrium statistics by greater than a predetermined threshold.

16. The method of claim 13, wherein the variant distribution statistics correspond to a group comprising single nucleotide polymorphisms, insertions of varying lengths, and deletions of varying lengths.

17. A method of aligning a received biological sequence and a stored biological reference sequence without compromising the reference sequence, the method comprising:

receiving one or more comparison sequences corresponding to a nucleic acid;

analyzing each comparison sequence for the presence of sequence anomalies associated with malicious activity enabled by alignment of the one or more comparison sequences with a reference sequence;

computing linkage disequilibrium statistics associated with the one or more received comparison sequences;

comparing the computed linkage disequilibrium statistics with corresponding linkage disequilibrium statistics associated with loci of the reference sequence;

implementing a classifier to determine whether the linkage disequilibrium statistics deviate from the comparison sequences in the database by more than a predetermined threshold; and rejecting the one or more comparison sequences if (a) a sequence anomaly is detected or (b) the computed linkage disequilibrium statistics computed therefrom are determined, by the classifier, from the comparison sequences in the database by more than the predetermined threshold.

* * * * *